US012767724B2

(12) United States Patent
Nomura et al.

(10) Patent No.: US 12,767,724 B2
(45) Date of Patent: Oct. 20, 2026

(54) METHOD OF TREATING CARCINOMATOUS PERITONITIS

(71) Applicants: PERSEUS PROTEOMICS INC., Tokyo (JP); NATIONAL UNIVERSITY CORPORATION GUNMA UNIVERSITY, Maebashi (JP)

(72) Inventors: Fumiko Nomura, Tokyo (JP); Tadashi Matsuura, Tokyo (JP); Lilin Zhang, Tokyo (JP); Yoichi Aikawa, Tokyo (JP); Takayuki Asao, Maebashi (JP); Takehiko Yokobori, Maebashi (JP)

(73) Assignees: PERSEUS PROTEOMICS INC., Tokyo (JP); NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 972 days.

(21) Appl. No.: 17/780,758

(22) PCT Filed: Nov. 27, 2020

(86) PCT No.: PCT/JP2020/044185

§ 371 (c)(1),
(2) Date: May 27, 2022

(87) PCT Pub. No.: WO2021/107082

PCT Pub. Date: Jun. 3, 2021

(65) Prior Publication Data

US 2023/0250180 A1 Aug. 10, 2023

(30) Foreign Application Priority Data

Nov. 27, 2019 (JP) ................................ 2019-213812

(51) Int. Cl.
*C07K 16/28* (2006.01)
*A61K 39/00* (2006.01)
*A61P 1/00* (2006.01)
*A61P 1/18* (2006.01)
*A61P 35/00* (2006.01)

(52) U.S. Cl.
CPC ............ *C07K 16/2881* (2013.01); *A61P 1/00* (2018.01); *A61P 1/18* (2018.01); *A61P 35/00* (2018.01); *A61K 2039/505* (2013.01); *C07K 2317/34* (2013.01); *C07K 2317/76* (2013.01)

(58) Field of Classification Search
CPC .. C07K 16/2881; A61P 1/18; A61K 2039/505
See application file for complete search history.

(56) References Cited

U.S. PATENT DOCUMENTS 9,593,165 B2 * 3/2017 Kurosawa .......... C07K 16/2881

FOREIGN PATENT DOCUMENTS

| | | | | |
|---|---|---|---|---|
| CN | 104797600 A | | 7/2015 | |
| EP | 2 918 603 A1 | | 9/2015 | |
| JP | 2018024651 | * | 1/2018 | .......... A61K 39/395 |
| WO | WO 2014/073641 A1 | | 5/2014 | |

OTHER PUBLICATIONS

Machine English Translation of JP2018024615. (Year: 2018).*
Castro-Mesa et al., Bases and foundations of the treatment of peritoneal carcinomatosis: Review article. Medicina Universitaria 18, 98-104, 2016. (Year: 2016).*
Chinese Office Action and Search Report for corresponding Chinese Application No. 202080082359.1, dated Jul. 27, 2023, with an English translation.
Iinuma et al., "Intracellular targeting therapy of cisplatin-encapsulated transferrin-polyethylene glycol liposome on peritoneal dissemination of gastric cancer," International Journal of Cancer, vol. 99, 2002, pp. 130-137.
Japanese Office Action for corresponding Japanese Application No. 2021-561536, dated Jun. 11, 2024, with English translation.
Extended European Search Report for corresponding European Application No. 20892360.7, dated Nov. 24, 2023.
Juhlin et al., "Clinical and Biochemical Effects In Vivo of Monoclonal Antitumor Antibody in Verner-Morrison's Syndrome," Cancer, vol. 73, 1994, pp. 1346-1352.
Yamada et al., "A new anticancer drug delivery system for the management of carcinomatous peritonitis," Original Communication, vol. 109, Issue 6, Jun. 1991, pp. 1-8, Abstract only, retrieved from https://www.surgjournal.com/article/0039-6060(91)90415-I/pdf.
Chinese Office Action and Search Report for corresponding Chinese Application No. 202080082359.1, dated Aug. 1, 2024, with English translation.
Fuling, "Dictionary of Modern Medicine," Shandong Science and Technology Press, May 30, 1990, 3 pages total.
Chinese Office Action for corresponding Chinese Application No. 202080082359.1, dated Jan. 31, 2024, with an English translation.
International Preliminary Report on Patentability issued in PCT/JP2020/044185 on May 17, 2022.
International Search Report and Written Opinion issued in PCT/JP2020/044185 on Jan. 19, 2021 with English translation.
Ogawa et al., International Journal of Clinical Oncology, 2002, 37(2), p. 34, PS30-4.

* cited by examiner

*Primary Examiner* — Elly-Gerald Stoica
(74) *Attorney, Agent, or Firm* — Birch, Stewart, Kolasch & Birch, LLP

(57) ABSTRACT

It is an object of the present invention to provide a therapeutic drug for carcinomatous peritonitis. According to the present invention, a therapeutic drug for carcinomatous peritonitis which comprises an antibody which recognizes a transferrin receptor, is provided.

7 Claims, 6 Drawing Sheets

Specification includes a Sequence Listing.

[Fig. 1]
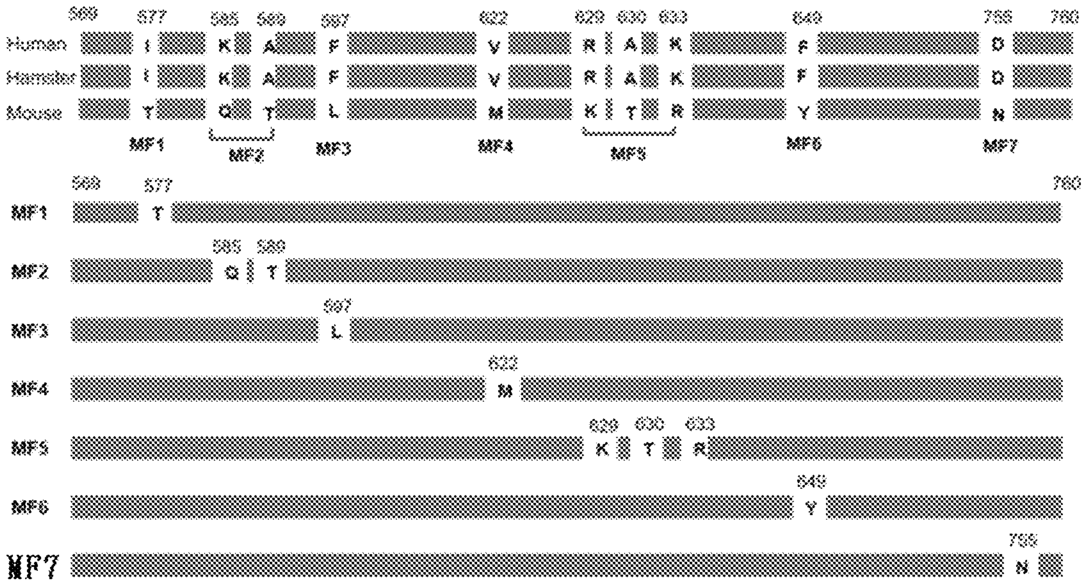

[Fig. 2]
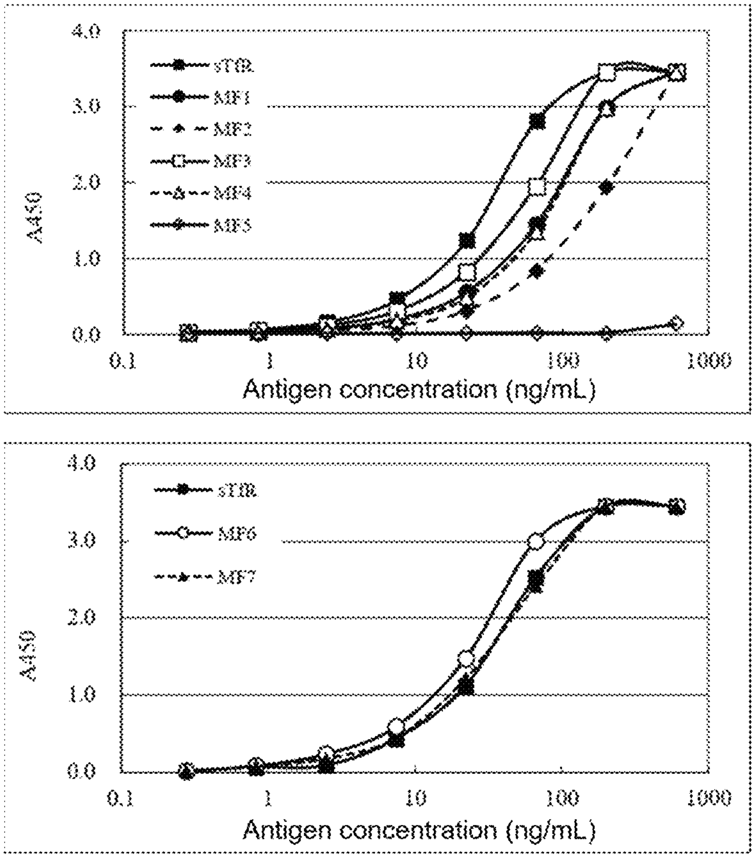

[Fig. 3]
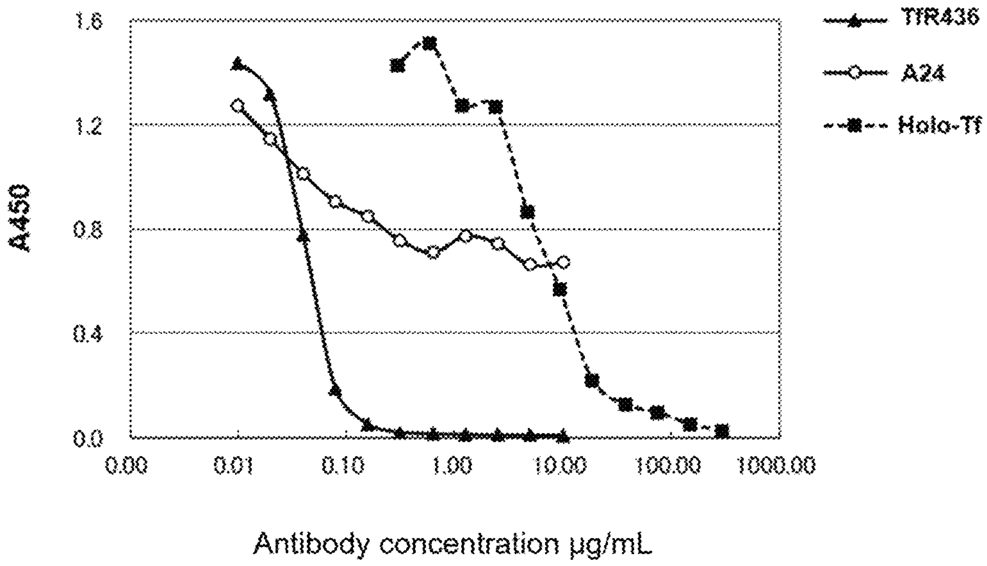
[Fig. 4]
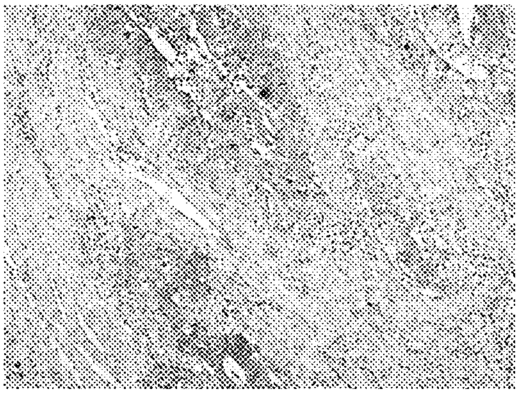
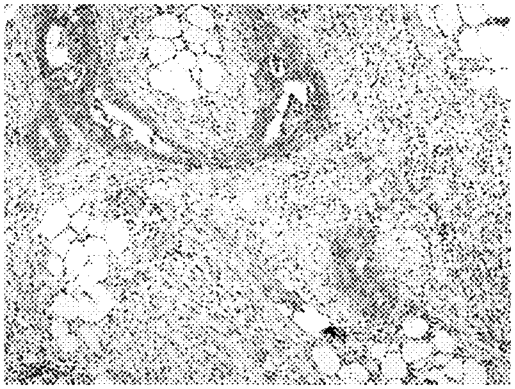
A. Primary tumor
B. Peritoneal disseminated tumor

[Fig. 5]
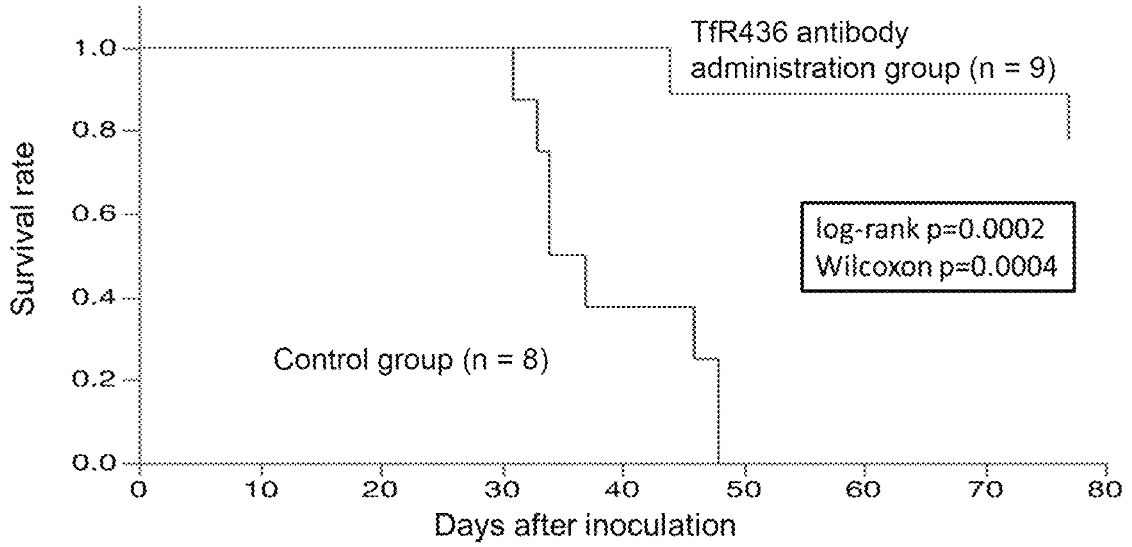
[Fig. 6]
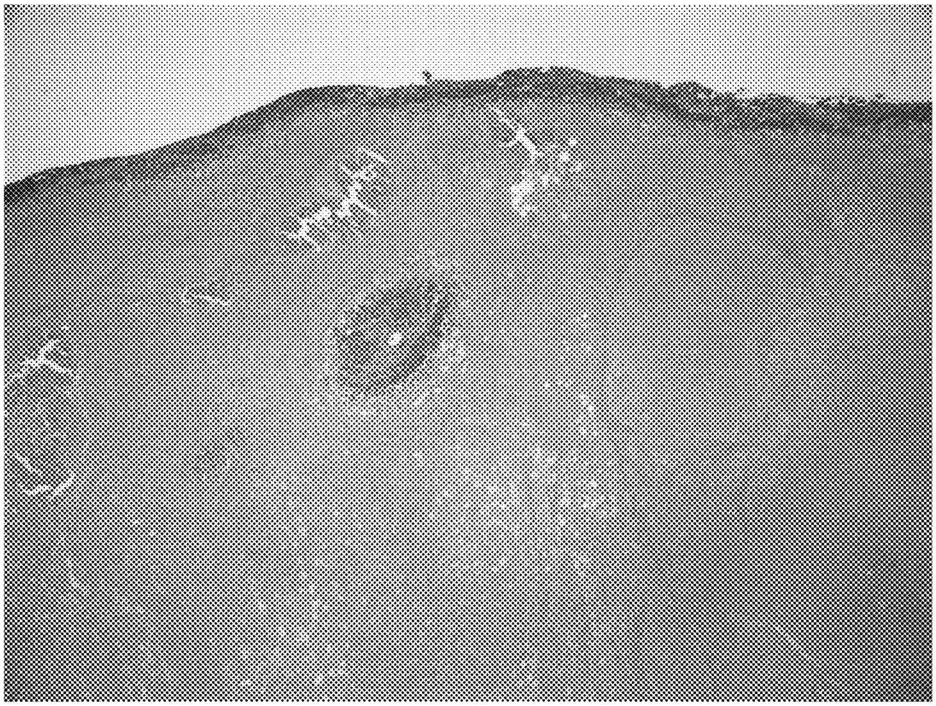

[Fig. 7]
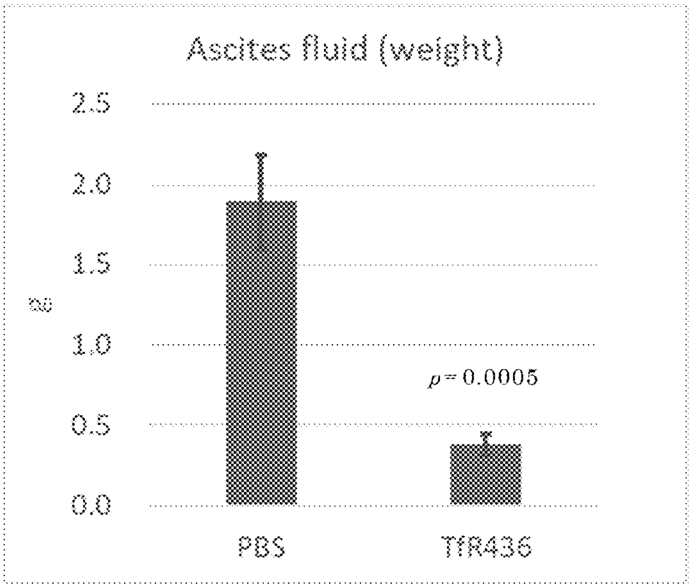
[Fig. 8]
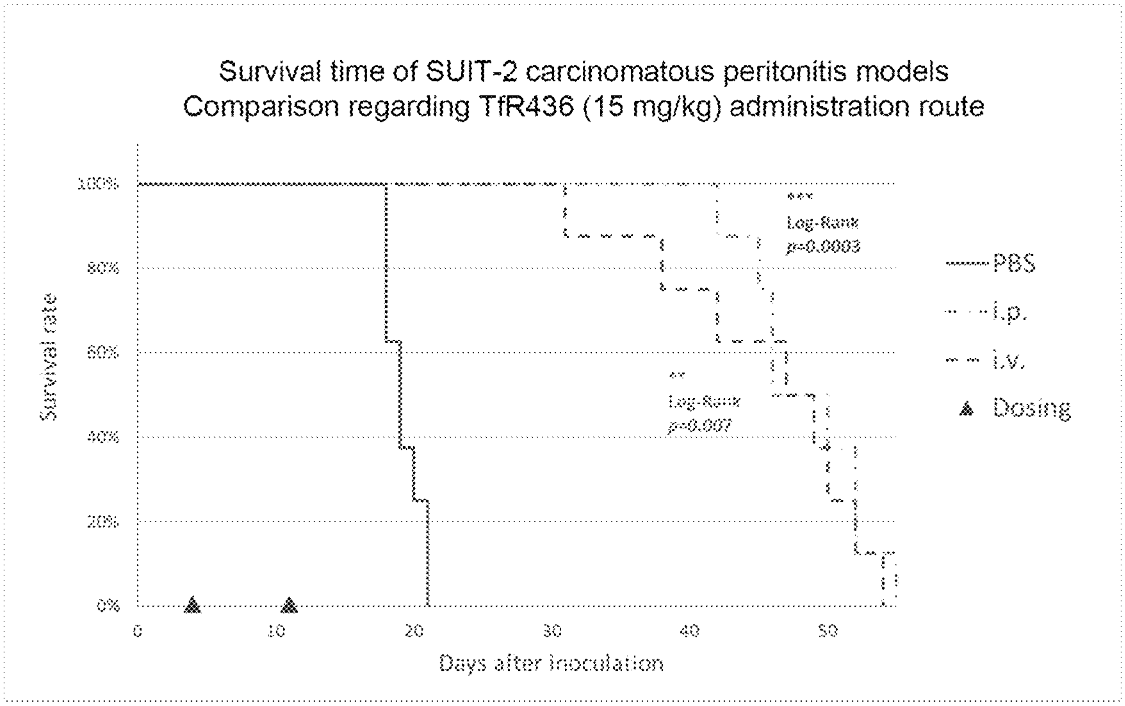

[Fig. 9]
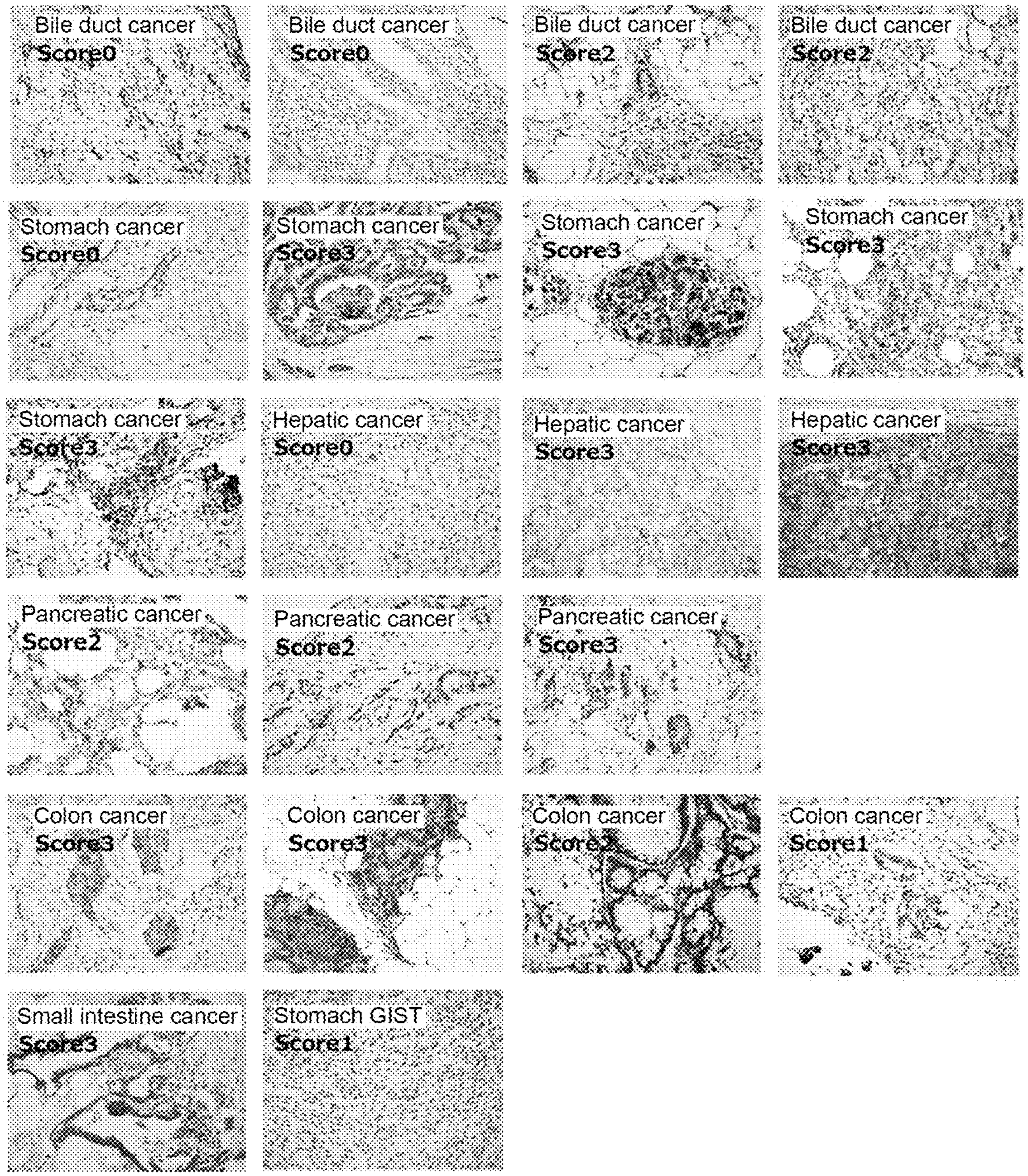

METHOD OF TREATING CARCINOMATOUS PERITONITIS

REFERENCE TO SEQUENCE LISTING SUBMITTED VIA EFS-WEB

This application includes an electronically submitted sequence listing in .txt format. The .txt file contains a sequence listing entitled "2022-11-18_2870-0804PUS1_ST25.txt" created on Nov. 18, 2022 and is 10,401 bytes in size. The sequence listing contained in this .txt file is part of the specification and is hereby incorporated by reference herein in its entirety.

TECHNICAL FIELD

The present invention relates to a therapeutic drug for carcinomatous peritonitis which comprises an anti-transferrin receptor antibody.

BACKGROUND ART

Transferrin receptor (TfR) has been identified to be a receptor that is present on a reticulocyte as a cell membrane structure for incorporating transferrin (Tf)-bound iron into a cell. Thereafter, it is discovered that TfR is expressed in placental trophoblasts, in activated lymphocytes, and further, in various tumor cells. For example, the high expression of TfR in breast cancer, prostate cancer, lung cancer, pancreatic cancer, colon cancer, stomach cancer, bladder cancer, hepatic cancer, cervical cancer, brain tumor, chronic lymphocytic leukemia, non-Hodgkin's lymphoma, and adult T-cell leukemia has been reported. Moreover, since TfR is expressed on the surface of various types of cancer cells at a high level and is expressed in normal cells at a low level, this receptor is recognized as a molecular target for cancer therapy. For example, Patent Document 1 discloses an antibody capable of specifically recognizing the transferrin receptor and an anti-cancer agent using the aforementioned antibody.

Carcinomatous peritonitis is a pathological condition, in which cancer has metastasized to the peritoneum. Carcinomatous peritonitis is likely to occur in all of cancer species, but the complication rate of carcinomatous peritonitis is high in gastrointestinal cancers occurring in the abdominal cavity (e.g. stomach cancer, pancreatic cancer, colon cancer, etc.) or in ovarian cancer.

PRIOR ART DOCUMENT

Patent Document

Patent Document 1: International Publication WO2014/073641

SUMMARY OF INVENTION

Object to be Solved by the Invention

It has been known that peritoneally metastasized cancer cells are special cells, which have acquired viability under hypoxic conditions. It is predicted that such peritoneally metastasized cancer cells have acquired resistance to anticancer agents, which target a normal cell growth mechanism. Even from a large number of clinical experiences or clinical trial results, it has been elucidated that intraperitoneal administration of ordinary anticancer agents is invalid to the treatment of carcinomatous peritonitis. Examples of the method for treating carcinomatous peritonitis may include immunotherapy and hyperthermic treatment, in addition to chemical treatment. However, the therapeutic effects obtained from these treatment methods are not sufficient and provide poor prognosis. Thus, it has been desired to develop a novel method for treating carcinomatous peritonitis. It is an object of the present invention to provide a therapeutic drug for carcinomatous peritonitis.

Means for Solving the Object

The present inventors have conducted studies directed towards achieving the aforementioned object. The present inventors have administered an antibody that recognizes the amino acid sequence at a certain position in TfR, to carcinomatous peritonitis mouse models. As a result, the inventors have found that carcinomatous peritonitis can be treated by administration of the aforementioned antibody, thereby completing the present invention.

Specifically, according to the present invention, the following inventions are provided.

(1) A therapeutic drug for carcinomatous peritonitis which comprises an antibody which recognizes a transferrin receptor.

(2) The therapeutic drug for carcinomatous peritonitis according to (1), wherein the antibody which recognizes a transferrin receptor is an antibody which recognizes a human transferrin receptor.

(3) The therapeutic drug for carcinomatous peritonitis according to (2), wherein the antibody which recognizes a human transferrin receptor is an antibody which recognizes the amino acids at positions 629 to 633 of the human transferrin receptor.

(4) The therapeutic drug for carcinomatous peritonitis according to any one of (1) to (3), wherein the antibody is an antibody having a heavy chain first complementarity determining region (VH CDR1), a heavy chain second complementarity determining region (VH CDR2), and a heavy chain third complementarity determining region (VH CDR3), which are as set forth in SEQ ID NOs: 1, 2, and 3, respectively, and also having a light chain first complementarity determining region (VL CDR1), a light chain second complementarity determining region (VL CDR2), and a light chain third complementarity determining region (VL CDR3), which are as set forth in SEQ ID NOs: 4, 5, and 6, respectively.

(5) The therapeutic drug for carcinomatous peritonitis according to any one of (1) to (4), wherein the antibody is an antibody having a heavy chain as set forth in SEQ ID NO: 7 and a light chain as set forth in SEQ ID NO: 8.

(6) The therapeutic drug for carcinomatous peritonitis according to any one of (1) to (5), wherein the antibody is a human antibody or a humanized antibody.

(7) The therapeutic drug for carcinomatous peritonitis according to any one of (1) to (6), wherein the antibody is an antibody fragment selected from the group consisting of Fab, Fab', $F(ab')_2$, a single-chain antibody (scFv), a bispecific antibody, a disulfide-stabilized V region (dsFv) and a peptide comprising CDR.

(8) The therapeutic drug for carcinomatous peritonitis according to any one of (1) to (7), wherein the carcinomatous peritonitis occurs in combination with cancer which causes the carcinomatous peritonitis.

(9) The therapeutic drug for carcinomatous peritonitis according to any one of (1) to (8), wherein the carcinomatous peritonitis occurs in combination with stomach cancer, pancreatic cancer, colon cancer, ovarian cancer, bile duct cancer, hepatic cancer, gastrointestinal stromal tumor (GIST), or small intestine cancer.

(10) The therapeutic drug for carcinomatous peritonitis according to any one of (1) to (9), which is intraperitoneally administered.

(A) There is provided a method for therapy of carcinomatous peritonitis which comprises administering an antibody which recognizes a transferrin receptor to a patient.

(B) An antibody which recognizes a transferrin receptor for use in the therapy of carcinomatous peritonitis.

(C) Use of an antibody which recognizes a transferrin receptor for production of a therapeutic drug for carcinomatous peritonitis.

Advantageous Effects of Invention

The therapeutic drug for carcinomatous peritonitis of the present invention is useful in the treatment of carcinomatous peritonitis. The therapeutic drug for carcinomatous peritonitis of the present invention is a molecular targeted drug, which targets a novel mechanism of attacking a root of supplying nutrients necessary for the metabolism of cells. The therapeutic drug for carcinomatous peritonitis of the present invention is an optimal approach method for existing anticancer agent-resistant peritoneal disseminated cells, which survive in a low oxygen/undernutrition environment, and the present therapeutic drug for carcinomatous peritonitis will lead to an original novel medical treatment.

BRIEF DESCRIPTION OF DRAWINGS

FIG. 1 shows the sites of individual TfR mutant fragments, at which point mutations are performed.

FIG. 2 shows the reactivity of TfR436 with soluble wild-type TfR (sTfR) and TfR mutant fragments.

FIG. 3 shows the Tf-TfR binding inhibitory activity of TfR436.

FIG. 4 shows the expression of TfR in the tumor tissues of patients.

FIG. 5 shows the results of the analysis of survival time.

FIG. 6 shows the HE specimen of the abdominal tumor of a mouse in a TfR436 antibody administration group.

FIG. 7 shows the measurement results of ascites fluid weight.

FIG. 8 shows the results obtained by analyzing the survival rate of peritoneal dissemination models of the pancreatic cancer cell line SUIT2.

FIG. 9 shows the expression of TfR in patient specimens.

EMBODIMENT OF CARRYING OUT THE INVENTION

Hereinafter, the present invention will be described in more detail.

Definitions and General Techniques

Unless otherwise specified in the present description, scientific terms used regarding the present invention have meanings that are generally understood by a person skilled in the art. In general, nomenclatures and techniques applied to the cell and tissue culture, molecular biology, immunology, microbiology, genetics, protein and nucleic acid chemistry, and hybridization, which are described in the present description, are well known in the present technical field, and thus, are commonly used.

The methods and techniques of the present invention are carried out in accordance with conventional methods that are well known in the present technical field, in such ways as described in a variety of general reference documents cited and discussed throughout the present description and more specific reference documents, unless otherwise specified.

TfR

In the case of humans, a transferrin receptor (TfR) is a single-pass transmembrane protein (SEQ ID NO: 9) comprising 760 amino acids, and it is encoded by human chromosome 3. This protein has also been known as a CD71 antigen, and it is considered that this protein is associated with incorporation of iron into cells and cell growth. The TfR of the present invention is not particularly limited in terms of structure. Thus, human TfR includes all of a monomer, a polymer, an intact form expressed on a cell membrane, a soluble form constituted in an extracellular region, a truncated form, a mutation form caused by genetic mutation, deletion, etc., and a form which has undergone posttranslational modification by phosphorylation or the like.

React and Reactivity

The terms "react" and "reactivity" have the same meanings in the present description, unless otherwise specified. That is, these terms mean that an antibody recognizes an antigen. The antigen used herein may be any of an intact TfR expressed on a cell membrane, a truncated form, and a soluble form. In addition, the antigen may be either a TfR having a three-dimensional structure or a modified TfR. Examples of a means for examining reactivity include flow cytometry (FACS), enzyme-linked immunosorbent assay (ELISA), Western blotting, microfluorescence measuring technique (FMAT), surface plasmon resonance (Biacore), immunostaining, and immunoprecipitation.

The antibody used in flow cytometry may be either an antibody labeled with a fluorescent substance such as FITC or with biotin, or an unlabeled antibody. A fluorescently-labeled avidin, a fluorescently-labeled anti-human immunoglobulin antibody, or the like is used, depending on the presence or absence of labeling of the antibody used and the type thereof. Reactivity can be evaluated by adding a sufficient amount of anti-TfR antibody (generally having a final concentration of 0.01 to 10 μg/mL) to an analyte, and then by comparing the obtained reactivity with the reactivity with a negative control antibody or a positive control antibody.

Antibody

In the present description, the following abbreviations (in the parentheses) are used in accordance with the customs, as necessary.

Heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

In the present description, the term "antibody" has the same definitions as immunoglobulin, and should be understood as generally known in the present technical field. Specifically, the term "antibody" is not limited by any given specific method for producing the antibody. For example, the term "antibody" includes, but is not limited to, a recombinant antibody, a monoclonal antibody, and a polyclonal antibody.

In the present description, the term "human antibody" is used to mean any given antibody, in which the sequences of a variable region and a constant region are human sequences. This term includes antibodies which have human sequences and are modified, for example, to remove cysteine which may cause a possible decrease in immunogenicity, an increase in affinity, and undesirable folding. This term also includes antibodies produced in non-human cells by recombination, which enable glycosylation which is not specific to human cells. These antibodies can be prepared in various ways.

In the present description, the term "humanized antibody" means a non-human-derived antibody, in which amino acid residues characteristic for a non-human antibody sequence are substituted with residues found in positions corresponding to those of a human antibody. This "humanization" process is considered to reduce the immunogenicity of the obtained antibody in human. It would be understood that a non-human-derived antibody can be humanized using a technique well known in the present technical field. Please refer to, for example, Winter et al., Immunol. Today 14:43-46 (1993). The target antibody can be produced by an engineering approach via a recombination DNA technique of substituting CH1, CH2, CH3, a hinge domain, and/or a framework domain with those of the corresponding human sequence. For example, WO92/02190, and U.S. Pat. Nos. 5,530,101, 5,585,089, 5,693,761, 5,693,792, 5,714,350 and 5,777,085 can be referred. In the present description, the term "humanized antibody" includes a chimeric human antibody and a CDR-grafted antibody, within the definitions thereof.

The sequence of a framework region (FR) in a variable region of the antibody is not particularly limited, unless it substantially affects the specific binding ability of the antibody to the corresponding antigen. The FR region of a human antibody is preferably used, but it is also possible to use FR regions of animal species other than humans (e.g. a mouse or a rat).

In one aspect, the antibody comprises a constant region as well as a variable region (e.g. IgG antibody). The sequence of such a constant region is not particularly limited. For example, the constant region of a known human antibody can be used. The heavy chain constant region (CH) of a human antibody is not particularly limited, as long as it belongs to a human immunoglobulin (hereinafter referred to as "hIg"). Those of hIgG class are preferable, and any one of subclasses belonging to hIgG class, such as hIgG1, hIgG2, hIgG3 or hIgG4, may be used. On the other hand, the light chain constant region (CL) of a human antibody is not particularly limited, as long as it belongs to hIg, and those of κ class or λ class can be used. In addition, constant regions of animal species other than humans (e.g. a mouse or a rat) can also be used.

In the present description, the term "modified body" or "modified antibody" is used to mean that the amino acid sequence of the variable region (CDR sequences and/or FR sequences) of a parent antibody comprises a substitution, deletion, addition and/or insertion of one or multiple amino acids.

In the present description, the "parent antibody" means a TfR436 antibody which has a VH comprising the amino acid sequence as set forth in SEQ ID NO: 7 and a VL comprising the amino acid sequence as set forth in SEQ ID NO: 8. In the amino acid sequence, one or several (for example, 1 to 8, preferably 1 to 5, more preferably 1 to 3, and particularly preferably 1 or 2) amino acids are deleted, added, substituted and/or inserted. As a method of preparing the amino acid sequence of an antibody having a binding ability to TfR, which has been well known to a person skilled in the art, a method of introducing a mutation into a protein has been known. For instance, such a skilled person could prepare a modified antibody functionally equivalent to an antibody having a TfR-binding activity by appropriately introducing a mutation into the amino acid sequence of the antibody having a TfR-binding activity according to a site-directed mutagenesis (Hashimoto-Gotoh, T, Mizuno, T, Ogasahara, Y, an DNA kagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Thus, an antibody comprising a mutation of one or several amino acids in the variable region or constant region of a parent antibody and having a binding activity to TfR can also be used.

In the present description, the phrase "an activity equivalent to the activity of the parent antibody" is used to mean that the TfR-binding activity of a certain antibody is equivalent to that of the parent antibody thereof. The term "equivalent" does not necessarily mean the same level of activity. The activity may be increased, or the activity may also be decreased, as long as the antibody has the activity. An antibody having a decreased activity may be an antibody having an activity that is, for example, 30% or more, preferably 50% or more, more preferably 80% or more, further preferably 90% or more, and particularly preferably 95% or more of the activity of the original antibody.

The term "binding activity" means the activity of an antibody to recognize an antigen. This antigen may be an intact TfR expressed on a cell membrane, a truncated form, or a soluble form. In addition, the antigen may be either a TfR having a three-dimensional structure or a modified TfR. Examples of a means for examining the binding activity include flow cytometry (FACS), enzyme-linked immunosorbent assay (ELISA), Western blotting, microfluorescence measuring technique (FMAT), and surface plasmon resonance (Biacore).

The Tf-TfR binding inhibitory activity of an antibody can be measured according to the method described in the after-mentioned "Example 2(2): Comparison between TfR436 antibody and antibodies of other companies in terms of Tf-TfR binding inhibition." A TfR solution is dispensed into a substrate (a 96-well plate, etc.) and is then left at rest to obtain a solid phase, and thereafter, blocking is carried out. Subsequently, an HRP-labeled Tf solution is dispensed into the substrate, and an antibody is further added thereto, so that they are allowed to react with each other at room temperature. Thereafter, the substrate is washed, and a coloring reagent (TMB, etc.) is then added thereto, so that they are allowed to react with each other. After that, the absorbance is measured using a plate reader. By performing the above-described operations, the Tf-TfR binding inhibitory activity of the antibody can be evaluated.

The antibody is not limited by its origin, and it may be an antibody derived from any animal, such as a human antibody, a mouse antibody, or a rat antibody. Also, the present antibody may be a chimeric antibody or a humanized antibody. In a preferred aspect, the antibody of the present invention is a human antibody.

The antibodies may be different from one another in terms of amino acid sequence, molecular weight, isoelectric point, the presence or absence of a sugar chain or the form thereof, etc., depending on the after-mentioned cells or hosts which produce the antibodies, or a purification method. For example, an antibody which undergoes a posttranslational modification on the amino acid sequence described in the present description is included in the present invention. Moreover, an antibody which undergoes a posttranslational modification on a site other than those for the known posttranslational modification is also included in the present invention. Furthermore, when the antibody is allowed to express in prokaryotic cells such as *Escherichia coli*, a methionine residue is added to the N-terminus of the amino acid sequence of the original antibody. Such an antibody may also be used in the present invention. An antibody which undergoes a posttranslational modification on a site other than those for the known posttranslational modification is also included in the present invention.

Production of Antibody (1) scFv Reacting with Antigen Using Phage Display Library The antibody can be prepared by several methods known in the present technical field. For example, using a phage display technique, a library comprising a repertoire of antibodies having various affinity for TfR can be provided. Subsequently, such a library can be screened to identify and isolate antibodies against TfR. Preferably, the phage library is a scFv phage display library which is generated using human VL and VH cDNA which has been prepared from mRNA isolated from human B cells. A method of preparing and screening such a library is known in the present technical field. A genetic substance is recovered from phage clones exhibiting reactivity which have been screened using TfR as an antigen. By analyzing the selected phage gene, the DNA sequences of VH and VL encoding the variable region of a human antibody binding to the antigen can be determined. Using this scFv sequence, IgG is prepared from scFv, so as to obtain a human antibody.

(2) Preparation of IgG from scFv (Preparation of Human Antibody)

An H chain or L chain expression vector is produced, and it is then allowed to express in a host cell. Thereafter, the secreted supernatant is recovered and is then purified, so as to obtain a human antibody. Alternatively, such a human antibody can also be obtained by allowing VH and VL to express in a single vector (tandem type). These methods are well known, and can be carried out with reference to WO92/01047, WO92/20791, WO93/06213, WO93/11236, WO93/19172, WO95/01438, WO95/15388, WO97/10354, etc.

Specifically, DNA encoding VH is ligated to another DNA molecule encoding a heavy chain constant region (CH1, CH2 and CH3), so as to obtain a full-length heavy chain gene. The sequence of a human heavy chain constant region gene is known in the present technical field (for example, Kabat, E. A. et al., (1991) Sequences of Proteins of Immunological Interest, $5^{th}$ edition, U. S. Department of Health and Human Services, NIH Publication No. 91-3242), and a DNA fragment including such a region can be obtained by standard PCR amplification. The heavy chain constant region may be the constant region of IgG1, IgG2, IgG3, IgG4, IgA, IgE, IgM or IgD. The most preferred constant region is that of IgG1 or IgG2. The constant region sequence of IgG1 may include any given various alleles or allotypes known to be generated among different individuals, such as Gm (1), Gm (2), Gm (3) or Gm (17). These allotypes correspond to a substitution of amino acids naturally-occurring in the constant region of IgG1.

DNA encoding VL is ligated to another DNA molecule encoding the light chain constant region CL, so as to obtain a full-length L chain gene (and a Fab light chain gene). The sequence of a human light chain constant region gene is known in the present technical field (for example, Kabat, E. A. et al., (1991) Sequences of Proteins of Immunological Interest, $5^{th}$ edition, U. S. Department of Health and Human Services, NIH Publication No. 91-3242), and a DNA fragment including such a region can be obtained by standard PCR amplification. The light chain constant region may be the constant region of κ or λ. The κ constant region may include any given various alleles known to be generated among different individuals, such as Inv (1), Inv (2) or Inv (3). The λ constant region may be derived from any one of the three λ genes.

The thus obtained DNA encoding an H chain or L chain is inserted into a vector to produce an expression vector, and the produced expression vector is then allowed to express in a host cell. Thereafter, the secreted supernatant is recovered and purified to obtain a human antibody. Examples of the expression vector include a plasmid, retrovirus, adenovirus, adeno-associated virus (AAV), plant viruses such as cauliflower mosaic virus or tobacco mosaic virus, a cosmid, YAC, and EBV-derived episome. An expression vector and an expression regulatory sequence are selected, so that they are suitable for a host cell used for expression. An antibody light chain gene and an antibody heavy chain gene can be inserted into different vectors, or the two genes can also be inserted into a single expression vector. An antibody gene is inserted into an expression vector by a standard method (for example, ligation of a complementary restriction site on an antibody gene fragment to a vector, or blunt-ended ligation applied when no restriction sites are present).

A favorable vector encodes a functionally completed human CH or CL immunoglobulin sequence having a suitable restriction site, which has been produced by an engineering approach such that any given VH or VL sequence can be easily inserted and then expressed therein, as described above. In such a vector, splicing generally takes place between a splice donor site in the inserted J region and a splice acceptor site preceding a human C domain, or such splicing also takes place in a splice region existing in a human CH exon. Polyadenylation and transcription termination take place in a natural chromosomal site downstream of a coding region. A recombinant expression vector can also encode a signal peptide which promotes the secretion of an antibody chain derived from a host cell. An antibody chain gene can be cloned into a vector, such that a signal peptide can be ligated in-frame to the amino terminus of an immunoglobulin chain. The signal peptide may be either an immunoglobulin signal peptide or a heterogeneous signal peptide (namely, it may be a non-immunoglobulin protein-derived signal peptide).

An expression vector used for the antibody of the present invention may also have sequences such as a sequence for regulating replication of the vector in a host cell (e.g. a replication origin) or a selective marker gene sequence, as well as an antibody gene and a regulatory sequence. The selective marker gene promotes selection of a host cell into which a vector has been introduced. For instance, the selective marker generally imparts resistance to drugs such as G418, hygromycin or methotrexate to a host cell into which the vector has been introduced. Preferred selective marker genes include a dihydrofolate reductase (DHFR) gene (used in selection/amplification of methotrexate as a dhfr-host cell), a neomycin phosphotransferase gene (used in selection of G418), and a glutamate synthase gene.

A host cell is transformed with an antibody gene expression vector produced by the above-described method. Any type of cell may be used as a host cell, as long as it can produce the present antibody. Examples of such a host cell include bacteria, yeast, animal cells, insect cells, and plant cells. Among these cells, animal cells are preferable. Examples of the animal cells include Chinese hamster ovary cells CHO/dhfr(−) and CHO/DG44, monkey-derived cells COS (A. Wright & S. L. Morrison, J. Immunol. 160, 3393-3402 (1998)), and SP2/O cells (mouse myeloma) (K. Motmans et al., Eur. J. Cancer Prev. 5, 512-5199 (1996), R. P. Junghans et al., Cancer Res. 50, 1495-1502 (1990)). For transformation, a lipofectin method (R. W. Malone et al., Proc. Natl. Acad. Sci. USA 86, 6007 (1989), P. L. Felgner et al., Proc. Natl. Acad. Sci. USA 84, 7413 (1987)), an electroporation method, a calcium phosphate method (F. L. Graham & A. J. van der Eb, Virology 52, 456-467 (1973)), a DEAE-Dextran method, and the like are preferably applied.

A transformant is cultured, and a human antibody is then separated from the cells of the transformant or a culture medium thereof. For separation/purification of the antibody, methods such as centrifugation, ammonium sulfate fractionation, salting-out, ultrafiltration, affinity chromatography, ion exchange chromatography and gel filtration chromatography can be used by appropriately combining them.

Antibody Fragments

An antibody fragment can be produced based on the present antibody, or based on the sequence information of a gene encoding the present antibody. Examples of the antibody fragment include Fab, Fab', $F(ab')_2$, scFv, and dsFv antibodies.

Fab is obtained by digesting IgG by papain in the presence of cysteine. It is an antibody fragment with a molecular weight of approximately 50,000, which is constituted with L chain and H chain variable regions, and an H chain fragment consisting of a CH1 domain and a portion of a hinge region. In the present invention, the above-described antibody can be obtained by papain digestion. In addition, Fab can also be prepared by incorporating DNA encoding a portion of the H chain and the L chain of the above-described antibody into a suitable vector, then performing transformation with the resulting vector, and then obtaining it from the transformant.

Fab' is an antibody fragment with a molecular weight of approximately 50,000, which is obtained by cleaving a disulfide bond between the H chains of the below-mentioned $F(ab')_2$. In the present invention, Fab' can be obtained by digesting the above-described antibody by pepsin, and then cleaving a disulfide bond with a reducing agent. In addition, as with Fab, Fab' can also be prepared by genetic engineering using DNA encoding the Fab'.

$F(ab')_2$ is an antibody fragment with a molecular weight of approximately 100,000, which is obtained by binding, via a disulfide bond, one fragment (Fab') constituted with L chain and H chain variable regions and an H chain fragment consisting of a CH1 domain and a portion of a hinge region, to the other fragment (Fab'). In the present invention, $F(ab')_2$ can be obtained by digesting the above-described antibody by pepsin. In addition, as with Fab, $F(ab')_2$ can also be prepared by genetic engineering using DNA encoding the $F(ab')_2$.

scFv is an antibody fragment obtained by ligating the C-terminus of one chain of Fv consisting of an H chain variable region and an L chain variable region to the N-terminus of the other chain thereof, using a suitable peptide linker, so as to form a single chain. $(GGGGS)_3$ having high flexibility can be used, for example, as such a peptide linker. For instance, DNA encoding the H chain variable region and L chain variable region of the above-described antibody and DNA encoding a peptide linker are used to construct DNA encoding a scFv antibody, and the thus constructed DNA is then incorporated into a suitable vector. Thereafter, scFv can be prepared from a transformant obtained by transformation with the aforementioned vector.

dsFv is an Fv fragment obtained by introducing a Cys residue into a suitable site in each of an H chain variable region and an L chain variable region, and then stabilizing the H chain variable region and the L chain variable region by a disulfide bond. The site in each chain, into which the Cys residue is to be introduced, can be determined based on a conformation predicted by molecular modeling. In the present invention, for example, a conformation is predicted from the amino acid sequences of the H chain variable region and L chain variable region of the above-described antibody, and DNA encoding each of the H chain variable region and the L chain variable region, into which a mutation has been introduced based on such prediction, is then constructed. The thus constructed DNA is incorporated into a suitable vector. Thereafter, dsFv can be then prepared from a transformant obtained by transformation with the aforementioned vector.

Further, it is also possible to ligate the scFv antibody to the dcFv antibody or the like using a suitable linker, or to fuse such an antibody fragment with streptavidin, so as to multimerize the antibody fragment.

Bispecific Antibody

The antibody may be a bispecific antibody.

Examples of the bispecific antibody may include bispecific $(mab)_2$ obtained by chemically crosslinking two molecules of monoclonal antibodies to each other, bispecific F(ab')2 obtained by chemically crosslinking two molecules of Fab fragments to each other, quadroma, bsDb (a bispecific diabody), scBsDb (a single-chain bispecific diabody), scBsTaFv (a single-chain bispecific tandem variable domain), Bite (a bispecific T cell Engager antibody), and DNL-F(ab)3 (docl-and-lock trivalent Fab) (Shim, H. Bispecific Antibodies and Antibody-Drug Conjugates for Cancer Therapy: Technological Considerations. Biomolecules 2020, 10, 360).

Pharmaceutical Composition and Preparation

A pharmaceutical composition and a preparation, which comprises the therapeutic drug for carcinomatous peritonitis of the present invention, are also included in the scope of the present invention.

The therapeutic drug for carcinomatous peritonitis of the present invention can be used to treat carcinomatous peritonitis.

Carcinomatous peritonitis is a pathological condition, in which cancer has metastasized to the peritoneum. Such carcinomatous peritonitis is not particularly limited, but may be carcinomatous peritonitis which occurs in combination with cancer which causes the carcinomatous peritonitis. More specifically, it may be carcinomatous peritonitis which occurs in combination with stomach cancer, pancreatic cancer, colon cancer, ovarian cancer, bile duct cancer, hepatic cancer, gastrointestinal stromal tumor (GIST), or small intestine cancer. In the case of carcinomatous peritonitis, cancer cells are dispersed in the abdominal cavity, a large number of sand grain tumor mass are formed in the peritoneum, and ascites fluid is accumulated.

A pharmaceutical composition and a preparation, which comprises the therapeutic drug for carcinomatous peritonitis of the present invention, preferably comprises a physiologically acceptable diluent or carrier, in addition to the antibody. The pharmaceutical composition or the preparation may also be a mixture with other drugs. Examples of a suitable carrier used herein may include a normal saline, a phosphate buffered saline, a phosphate buffered saline with glucose, and a buffered saline, but the examples are not limited thereto. Otherwise, the antibody is freeze-dried, and when needed, the aforementioned buffered aqueous solution may be added thereto to reconstitute the antibody, and the thus reconstituted antibody may be then used. The dosage form may be, for example, parenteral administration such as intraperitoneal administration (e.g. intraperitoneal injection, etc.).

The applied dose of the therapeutic drug for carcinomatous peritonitis of the present invention is different depending on symptom, age, body weight, etc. In general, in the case of oral administration, the present pharmaceutical composition is administered at a dose of approximately 0.01 mg to 1,000 mg per day per adult, in terms of the amount of an antibody contained therein. Such a dose can be administered once or divided over several administrations per day. On the other hand, in the case of parenteral administration, the present pharmaceutical composition can be intraperitoneally administered at a dose of approximately 0.01 mg to 3,000 mg for a single administration.

The present invention will be described in more detail in the following examples. However, these examples are not intended to limit the scope of the present invention.

EXAMPLES

In the following examples, the TfR436 antibody described in paragraphs 0090 and 0091 of International Publication WO2014/073641 was used.

The CDR sequences of the TfR436 antibody will be shown below.

```
VH CDR1:
                              (SEQ ID NO: 1)
SYGMH

VH CDR2:
                              (SEQ ID NO: 2)
VISYDGSNKYYADSVKG

VH CDR3:
                              (SEQ ID NO: 3)
DSNFWSGYYSPVDV

VL CDR1:
                              (SEQ ID NO: 4)
TRSSGSIASNSVQ
```

-continued

```
VL CDR2:
                              (SEQ ID NO: 5)
YEDTQRPS

VL CDR3:
                              (SEQ ID NO: 6)
QSYDSAYHWV
```

The VH sequence and VL sequence of the TfR436 antibody will be shown below.

```
TfR436 VH
                                        (SEQ ID NO: 7)
DVQLVQSGGGVVQPGRSLRLSCAASGFPFKSYGMHWVRQAPGKGLEWVA

VISYDGSNKYYADSVKGRFTISRDNSKNTLYLQMNSLRGEDTAVYYCAR

DSNEWSGYYSPVDVWGQGTTVTVSS

TfR436 VL
                                        (SEQ ID NO: 8)
NFMLTQPHSVSESPGKTVTISCTRSSGSIASNSVQWYQQRPGSAPITVI

YEDTQRPSGVPDRFSGSIDSSSNSASLTISGLQTEDEADYYCQSYDSAY

HWVFGGGTKLAVL
```

Example 1: Identification of Binding Site of TfR436 Antibody

The TfR436 antibody did not cross-react with mouse TfR, but it exhibited cross-reactivity with hamster TfR. The amino acid sequence of a transferrin (TF)-binding site (the amino acids at positions 569 to 760) in TfR was aligned. The amino acids of a human TfR sequence, which were the same as hamster but were different from mouse, were picked up. The picked amino acids were subjected to point mutation, as shown in FIG. 1, so that soluble TfR mutant fragments were produced.

(1) Production of Soluble Wild-Type TfR (sTfR) and TfR Mutant Fragments (MF1 to MF7)

A human TfR extracellular domain (the amino acids at positions 89 to 760) or each TfR mutant fragment (MF1 to MF7) as shown in FIG. 1, and a nucleotide sequence encoding AAARGGPEQKLISEEDLNSAVDHHHHHH (SEQ ID NO: 10) were totally synthesized. A neomycin resistance gene and a DHFR gene were incorporated into the expression vector pCAGGS (Non-Patent Document 2.: Niwa et al. 1991), and thereafter, the synthesized genes were each inserted into the multicloning site of the obtained expression vector, so as to produce a pCAGGS-Neo-DHFR-sTFR-myc-his expression plasmid. Using Expifectamine (Invitrogen), the Expi293 cells (Invitrogen) were transfected with the above-described plasmid, and were then cultured at 37° C. in 8% $CO_2$ at 135 rpm for 5 days. Thereafter, a culture supernatant was recovered by centrifugation. A HisTrapHP (GE Healthcare) column was connected with AKTA prime (GE Healthcare), and sTfR or MF1 to MF7 were then purified using 20 mM Imidazole/DPBS as a binding buffer and 500 mM Imidazole/DPBS as an elution buffer. The eluted protein was subjected to buffer exchange with 30 mM HEPES, 5% trehalose, pH 7.2, by using a Zeba spin column (Thermo scientific).

(2) Identification of Binding Site of TfR436 Antibody

The thus purified sTfR or MF1 to MF7 were diluted with PBST (Phosphate Buffered Saline with Tween 20, TaKaRa), and the diluted solutions were prepared at 7 stages by 3-fold dilution from 600 ng/ml. Thereafter, the diluted solution was dispensed into Ni-NTA HisSorb Strips 96-well plate (QIAGEN) in an amount of 100 μL/well, and the plate was then placed on a shaker, followed by performing a reaction at room temperature. One hour later, the reaction mixture was washed with PBST Buffer 5 times, and the TfR436 antibody (1 μg/mL) was dispensed into the 96-well plate in an amount of 100 μL/well. The plate was placed on a shaker, and a reaction was then performed at room temperature for 1 hour. Thereafter, the reaction mixture was washed with PBS-T Buffer 5 times, and a 50,000-fold diluted secondary antibody, F(ab')2 Fragment Anti-Human IgG Fcγ (Jackson Immuno Research), was then dispensed into the 96-well plate in an amount of 100 μL/well, followed by performing a reaction at room temperature for 1 hour. The reaction mixture was washed with PBST Buffer 5 times, and TMB Soluble Reagent (High Sensitivity) (Scy Tek) was then dispensed into the plate in an amount of 100 μL/well, followed by performing a reaction at room temperature in a dark place for 3 minutes. After that, TMB Stop Buffer (Scy Tek) was added to the plate in an amount of 100 μL/well, and the obtained mixture was then shaken using a shaker for 1 minute. Thereafter, the absorbance at 450 nm (ref. 620 nm) was measured using a plate reader.

As a result, as shown in FIG. 2, a reduction in the reactivity of the TfR436 antibody with the TfR mutant fragment MF5 was observed, but a reduction in the reactivity of the TfR436 antibody with other mutant fragments was not observed. That is to say, when the amino acids at positions 629, 630 and 633 of TfR are substituted with other amino acids, the TfR436 antibody cannot recognize the TfR. Thus, it was suggested that the amino acids at positions 629 to 633 of TfR should be an epitope recognized by the TfR436 antibody.

Example 2: Comparison Between TfR436 Antibody and Comparative Antibodies in Terms of Tf-TfR Binding Inhibition (1) Production of Comparative Antibody A24

Patent Document US2008/0193453 discloses an A24 antibody reacting against human TfR. In order to compare the TfR436 antibody with the A24 antibody, the deposited hybridomas were acquired, and the antibody was produced. Specifically, the hybridomas were seeded into RPMI1640 (GIBCO) supplemented with 10% FBS at a cell concentration of 1 to $2\times10^5$/mL, and were then cultured in a 5% $CO_2$ incubator at 37° C. After completion of an expansion culture, the cells were recovered by centrifugation, and were then washed with PBS twice. Thereafter, the resulting cells were further subjected to an expansion culture in a serum-free medium Cosmedium 005 (Cosmo Bio Co., Ltd.) and 0.5% Nutridoma-CS (Roche) to result in a volume of 550 mL. Five days after the cells became confluent, a culture supernatant was recovered by centrifugation.

The recovered supernatant was applied onto a protein A carrier (Ab-Capcher ExTra: ProteNova), and an antibody binding to protein A was eluted with a 0.1 M glycine-HCl buffer (pH 2.7), and then, was rapidly neutralized with a 1 M Tris-HCl buffer (pH 8.5). Thereafter, using an Ultracell Ultrafiltration Disk (Merck Millipore), the buffer was exchanged with PBS.

(2) Comparison Between TfR436 Antibody and Antibodies of Other Companies in Terms of Tf-TfR Binding Inhibition The sTfR described in Example 1 was adjusted to a concentration of 5.0 μg/mL by addition of PBST, and the diluted solution was then dispensed into MaxiSorp 96-well plate (Nunc) in an amount of 100 μL/well. Thereafter, it was left at rest at 4° C. overnight to obtain a solid phase. On the following day, the solid phase solution was discarded, and 100% Block Ace (DS Pharma Biomedical) was added to the plate in an amount of 200 μL/well, followed by leaving the obtained mixture at rest at room temperature so as to carry out blocking. One hour later, the reaction mixture was washed with PBST Buffer 5 times, and HRP-labeled Tf (2 μg/mL) was then dispensed into the plate in an amount of 50 μL/well. Thereafter, the TfR436 antibody, the A24 antibody (2-fold dilution series from 10 μg/mL), or holo-Tf (Sigma) (2-fold dilution series from 300 μg/mL) was further added to the mixture in an amount of 50 μL/well. The obtained mixture was reacted at room temperature for 1 hour, and was then washed with PBST Buffer 5 times. Thereafter, TMB Soluble Reagent (High Sensitivity) was dispensed into the plate in an amount of 100 μL/well, and the obtained mixture was then reacted at room temperature in a dark place. Twenty five minutes later, TMB Stop Buffer was added to the plate in an amount of 100 μL/well, and the obtained mixture was shaken with a shaker for 1 minute. Thereafter, the absorbance at 450 nm (ref. 620 nm) was measured.

As a result, as shown in FIG. 3, the TfR436 antibody completely inhibited the binding of Tf-TfR at a significantly low dose (100 ng/ml). In contrast, the A24 antibody could not completely inhibit the binding of Tf-TfR, even though it was used at a dose of 10 μg/mL, and could inhibit only 50% of the Tf-TfR binding. Thus, it was suggested that the TfR436 antibody is excellent in terms of inhibition of the Tf-TfR binding.

Example 3: Expression of TfR in Specimens of Carcinomatous Peritonitis Patients (Immunostaining of Patient Pathological Specimens)

The expression of TfR1 in the tumor tissues of a primary focus and a peritoneal dissemination focus collected from patients with carcinomatous peritonitis which was derived from stomach cancer as primary cancer was studied by immunostaining. A tumor tissue slide was deparaffinized, and was then subjected to antigen activation in an activation buffer with pH 6.0 at 121° C. for 15 minutes using an autoclave. The resultant was subjected to endogenous peroxidase treatment with 0.3% $H_2O_2$ water, and was then reacted with a primary antibody (0.4 μg/mL Anti TFRC Rabbit, ATLAS ANTIBODIES, HPA028598) at 4° C. overnight. Thereafter, the resultant was washed with PBS, and was then reacted with a polymer reagent (Histofine Simple Stain MAX-PO MULTI, NICHIREI CORPORATION, 424152) at room temperature for 30 minutes, followed by washing with PBS. The resultant was colored with a DAB reagent (Histofine Simple Stain DAB, NICHIREI CORPORATION, 415172). The nucleus was stained with hematoxylin, and the resultant was then subjected to dehydration, penetration, and enclosing, so as to obtain an immunostained specimen.

As a result, as shown in FIG. 4, the expression of TfR was confirmed in both the stomach cancer patient primary focus-derived tumor tissues (FIG. 4A) and the peritoneal dissemination focus tumor tissues (FIG. 4B).

Example 4: Antitumor Effects Found in Stomach Cancer Cell Line MKN45-Luc Peritoneal Dissemination Models Using stomach cancer cell line MKN45-Luc peritoneal dissemination models, the antitumor effects of a TfR436 antibody was studied.

The MKN45-Luc cell line (JCRB1379) was cultured in a culture medium (RPMI-1640, 10% FBS, 1% P/S). The culture medium was removed, and the cells were then washed with PBS once. Thereafter, the cells were peeled using TrypLE Express. The cells were recovered by addition of the culture medium, and were then washed with PBS once. The resulting cells were suspended in PBS again, and the number of the cells was then counted using 0.4% Trypan blue. After completion of the cell counting, the cell density was adjusted to $1\times10^7$/mL with PBS. This cell suspension was drawn into a 1 mL tuberculin syringe, and a two-step needle was then equipped into the syringe. The cell suspension was transplanted into the abdominal cavity of twenty C.B-17/IcrHsd-Prkdc$^{scid}$ mice (female, 6-week-old at the arrival) in an amount of 200 μL/mouse. The number of the transplanted cells was $2\times10^6$ cells/mouse.

Three days after the transplantation, 500 μg of luciferin was intraperitoneally administered to the mice, and light emission from the transplanted cells was then measured. Among the 20 transplanted mice, the survival of the transplanted cells was confirmed in 17 mice by detection of the light emission. The 17 mice were divided into groups (control group: 8 mice; and antibody administration group: 9 mice) depending on the intensity of the emitted light. Thereafter, the drug was intraperitoneally administered to the mice once a week, a total of 4 administrations. PBS was administered to the control group, whereas 15 mg/kg TfR436 antibody was administered to the antibody administration group.

The mice were observed during the test period, and viability was examined. On Day 77 after the transplantation, the test was terminated, and statistical analysis was then carried out based on the survival time of the mice. As a result, it was confirmed that the TfR436 antibody administration group exhibited significant life-extending effects (Log-Rank (p=0.0002) and Wilcoxon (p=0.0004)), in comparison to the control group (FIG. 5). In addition, it was also confirmed that a tumor mass was formed in the abdominal cavity of 7 mice in the TfR436 antibody administration group, which survived at the time of termination of the test. Such a tumor mass was collected, and a pathological specimen was produced therefrom. As a result, necrosis was observed in a broad range of the tumor mass, and tumor cells having proliferating ability remained only in a few regions of the surface of the tumor mass and around the blood vessels (FIG. 6).

Examples 5: Studies Regarding Antitumor Effects Using Pancreatic Cell Line SUIT-2 Peritoneal Dissemination Models The SUIT-2 cell line (JCRB1094) was cultured in a culture medium (EMEM, 10% FBS, 1% P/S). The culture medium was removed, and the cells were then washed with PBS once. Thereafter, the cells were peeled using TrypLE Express. The cells were recovered by addition of the culture medium, and were then washed with PBS once. The resulting cells were suspended in PBS again, and the number of the cells was then counted using 0.4% Trypan blue. After completion of the cell counting, the cell density was adjusted to $1\times10^7$/mL with PBS. This cell suspension was drawn into a 1 mL tuberculin syringe, and a two-step needle was then equipped into the syringe. The cell suspension was transplanted into the abdominal cavity of thirty C.B-17/IcrHsd-Prkdc$^{scid}$ mice (female, 6-week-old at the arrival) in an amount of 200 μL/mouse. The number of the transplanted cells was $2\times10^6$ cells/mouse.

The cell survival rate after the transplantation was 100% in the present models (from the results of a preliminary test). Thus, 4 days after the cell transplantation, random assignment was carried out based on body weight (a control group and an antibody administration group; n=10). Thereafter, the drug was intraperitoneally administered to the mice once a week, a total of 2 administrations. PBS was administered to the control group, whereas 15 mg/kg TfR436 antibody was administered to the antibody administration group. During the test period, the measurement of the body weight of the mice and observation thereof were carried out, and on Day 17 after the transplantation, on which deterioration of the systemic condition of the control group mice was confirmed due to an increase in peritoneal disseminated tumors, the test was terminated. The mice in the two groups were subjected to euthanasia, and thereafter, collection of ascites fluid and observation of intraperitoneal tumor mass were carried out. With regard to the weight of ascites fluid, the control group was compared with the TfR436 antibody administration group according to a t-test. The measurement results of the ascites fluid weight are shown in FIG. 7. As a result, a significant reduction in the ascites fluid weight (P=0.0005) was confirmed in the TfR436 antibody administration group. Moreover, in the observation of the intraperitoneal tumor mass, it was found that a plurality of tumor mass were formed on the mesentery of the mice in the control group. On the other hand, in the TfR436 antibody administration group, 1 or 2 tumor masses were observed in 4 mice, but clear tumor mass formation was not observed in 6 mice.

Example 6: Life-Extending Effects Found in Pancreatic Cancer Cell Line SUIT2 Peritoneal Dissemination Models The SUIT-2 cell line (JCRB1094) was cultured in a culture medium (EMEM, 10% FBS, 1% P/S). The culture medium was removed, and the cells were then washed with PBS once. Thereafter, the cells were peeled using TrypLE Express. The cells were recovered by addition of the culture medium, and were then washed with PBS once. The resulting cells were suspended in PBS again, and the number of the cells was then counted using 0.4% Trypan blue. After completion of the cell counting, the cell density was adjusted to $1\times10^7$/mL with PBS. This cell suspension was drawn into a 1 mL tuberculin syringe, and a two-step needle was then equipped into the syringe. The cell suspension was transplanted into the abdominal cavity of twenty-five C.B-17/IcrHsd-Prkdc$^{scid}$ mice (female, 7-week-old at the arrival) in an amount of 200 μL/mouse. The number of the transplanted cells was $2\times10^6$ cells/mouse.

The cell survival rate after the transplantation was 100% in the present models (from the results of a preliminary test). Thus, 4 days after the cell transplantation, random assignment was carried out based on body weight (a control group, an antibody intraperitoneal administration group, and an antibody intravenous administration group; n=8). Thereafter, the drug was administered to the mice once a week, a total of 2 administrations. That is, PBS was administered to the control group, whereas 15 mg/kg TfR436 antibody was administered to the antibody administration groups. Until Day 55 after the cell transplantation, the measurement of the body weight of the mice and observation of the systemic condition thereof were carried out. At the time point, in which deterioration of the systemic condition due to an increase in tumors (e.g. excessive accumulation of ascites fluid, anemia, and weakness) was confirmed, the mice were subjected to euthanasia. The number of days elapsed from the cell transplantation until euthanasia was defined as a survival period. The survival period from Day 55 after the transplantation was subjected to Log-Rank analysis. As a result, it was confirmed that the TfR436 antibody administration groups exhibited significant life-extending effects (intraperitoneal administration group (p=0.0003); and intravenous administration group (p=0.007)), in comparison to the PBS group, and further that the medicinal effects obtained by intraperitoneal administration were superior to the medicinal effects obtained by intravenous administration (FIG. 8).

Example 7: Analysis of TfR Expression in Patient Specimens

Using the specimens of cancer patients shown in the following table, the TfR expression state was analyzed by immunostaining of only the peritoneal disseminated tumors according to the same method as that of Example 3. Determination criteria are shown in Table 1.

TABLE 1

| Score | Determination Criteria |
|---|---|
| 0 | Cell membrane is not positively stained. |
| 1 | Cell membrane is slightly stained. |
| 2 | Cell membrane is stained at a low to moderate level. |
| 3 | Cell membrane is strongly stained. |

The results are shown in Table 2 and FIG. 9.

TABLE 2

| | Score 0 Negative | Score 1 Weakly positive | Score 2 Moderately positive | Score 3 Strongly positive | Expression positive rate |
|---|---|---|---|---|---|
| Bile duct cancer (4 cases) | 2 | 0 | 2 | 0 | 50% |
| Stomach cancer (5 cases) | 1 | 0 | 0 | 4 | 80% |
| Hepatic cancer (3 cases) | 1 | 0 | 0 | 2 | 67% |
| Pancreatic cancer (3 cases) | 0 | 0 | 2 | 1 | 100% |
| Colon cancer (4 cases) | 0 | 1 | 1 | 2 | 100% |
| Rare cancer (2 cases) | 0 | 1 (GIST) | 0 | 1 (Small intestine cancer) | 100% |

The invention claimed is:

1. A method for treating carcinomatous peritonitis in a patient, comprising:

intraperitoneally or intravenously administering to the patient a therapeutically effective amount of a drug comprising an antibody which recognizes the amino acids at positions 629 to 633 of a human transferrin receptor, wherein the antibody is an antibody having a heavy chain first complementarity determining region (VH CDR1), a heavy chain second complementarity determining region (VH CDR2), and a heavy chain third complementarity determining region (VH CDR3), which are as set forth in SEQ ID NOs: 1, 2, and 3, respectively, and also having a light chain first complementarity determining region (VL CDR1), a light chain second complementarity determining region (VL CDR2), and a light chain third complementarity determining region (VL CDR3), which are as set forth in SEQ ID NOs: 4, 5, and 6, respectively.

2. The method according to claim 1, wherein the antibody is an antibody having a heavy chain as set forth in SEQ ID NO: 7 and a light chain as set forth in SEQ ID NO: 8.

3. The method according to claim 1, wherein the antibody is a human antibody or a humanized antibody.

4. The method according to claim 1, wherein the antibody is an antibody fragment selected from the group consisting of Fab, Fab', $F(ab')_2$, a single-chain antibody (scFv), a bispecific antibody, a disulfide-stabilized V region (dsFv) and a peptide comprising CDR.

5. The method according to claim 1, wherein the carcinomatous peritonitis occurs in combination with cancer which causes the carcinomatous peritonitis.

6. The method according to claim 1, wherein the carcinomatous peritonitis occurs in combination with stomach cancer, pancreatic cancer, colon cancer, ovarian cancer, bile duct cancer, hepatic cancer, gastrointestinal stromal tumor (GIST), or small intestine cancer.

7. The method according to claim 1, wherein the therapeutic drug is intraperitoneally administered.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Homo sapiens

<400> SEQUENCE: 1

Ser Tyr Gly Met His
1               5


<210> SEQ ID NO 2
<211> LENGTH: 17
<212> TYPE: PRT
<213> ORGANISM: Homo sapiens

<400> SEQUENCE: 2

Val Ile Ser Tyr Asp Gly Ser Asn Lys Tyr Tyr Ala Asp Ser Val Lys
1               5                   10                  15

Gly


<210> SEQ ID NO 3
<211> LENGTH: 14
<212> TYPE: PRT
<213> ORGANISM: Homo sapiens

<400> SEQUENCE: 3

Asp Ser Asn Phe Trp Ser Gly Tyr Tyr Ser Pro Val Asp Val
1               5                   10


<210> SEQ ID NO 4
<211> LENGTH: 13
<212> TYPE: PRT
<213> ORGANISM: Homo sapiens

<400> SEQUENCE: 4
```

Thr Arg Ser Ser Gly Ser Ile Ala Ser Asn Ser Val Gln
1 5 10

<210> SEQ ID NO 5
<211> LENGTH: 8
<212> TYPE: PRT
<213> ORGANISM: Homo sapiens

<400> SEQUENCE: 5

Tyr Glu Asp Thr Gln Arg Pro Ser
1 5

<210> SEQ ID NO 6
<211> LENGTH: 10
<212> TYPE: PRT
<213> ORGANISM: Homo sapiens

<400> SEQUENCE: 6

Gln Ser Tyr Asp Ser Ala Tyr His Trp Val
1 5 10

<210> SEQ ID NO 7
<211> LENGTH: 123
<212> TYPE: PRT
<213> ORGANISM: Homo sapiens

<400> SEQUENCE: 7

Asp Val Gln Leu Val Gln Ser Gly Gly Gly Val Val Gln Pro Gly Arg
1 5 10 15

Ser Leu Arg Leu Ser Cys Ala Ala Ser Gly Phe Pro Phe Lys Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Gly Glu Asp Thr Ala Val Tyr Tyr Cys
85 90 95

Ala Arg Asp Ser Asn Phe Trp Ser Gly Tyr Tyr Ser Pro Val Asp Val
100 105 110

Trp Gly Gln Gly Thr Thr Val Thr Val Ser Ser
115 120

<210> SEQ ID NO 8
<211> LENGTH: 111
<212> TYPE: PRT
<213> ORGANISM: Homo sapiens

<400> SEQUENCE: 8

Asn Phe Met Leu Thr Gln Pro His Ser Val Ser Glu Ser Pro Gly Lys
1 5 10 15

Thr Val Thr Ile Ser Cys Thr Arg Ser Ser Gly Ser Ile Ala Ser Asn
20 25 30

Ser Val Gln Trp Tyr Gln Gln Arg Pro Gly Ser Ala Pro Ile Thr Val
35 40 45

Ile Tyr Glu Asp Thr Gln Arg Pro Ser Gly Val Pro Asp Arg Phe Ser
50 55 60

Gly Ser Ile Asp Ser Ser Ser Asn Ser Ala Ser Leu Thr Ile Ser Gly

```
65                  70                  75                  80

Leu Gln Thr Glu Asp Glu Ala Asp Tyr Tyr Cys Gln Ser Tyr Asp Ser
                85                  90                  95

Ala Tyr His Trp Val Phe Gly Gly Gly Thr Lys Leu Ala Val Leu
            100                 105                 110


<210> SEQ ID NO 9
<211> LENGTH: 760
<212> TYPE: PRT
<213> ORGANISM: Homo sapiens

<400> SEQUENCE: 9

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335
```

```
Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
```

-continued

```
        755                 760


<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Recombinant
      tag

<400> SEQUENCE: 10

Ala Ala Ala Arg Gly Gly Pro Glu Gln Lys Leu Ile Ser Glu Glu Asp
1               5                   10                  15

Leu Asn Ser Ala Val Asp His His His His His His
            20                  25
```